United States Patent [19]

Kulsa et al.

[11] 4,130,661

[45] Dec. 19, 1978

[54] SUBSTITUTED BENZOYLACRYLANILIDES

[75] Inventors: Peter Kulsa, Plainfield; Dale R. Hoff, Basking Ridge; Helmut H. Mrozik, Matawan, all of N.J.

[73] Assignee: Merck & Co., Inc., Rahway, N.J.

[21] Appl. No.: 812,027

[22] Filed: Jun. 30, 1977

Related U.S. Application Data

[63] Continuation of Ser. No. 629,438, Nov. 6, 1975, abandoned, which is a continuation-in-part of Ser. No. 521,708, Nov. 7, 1974, abandoned, which is a continuation-in-part of Ser. No. 416,134, Nov. 15, 1973, abandoned.

[51] Int. Cl.$^2$ .................. C01B 33/00; C07C 103/22; C07C 103/28; C07C 103/38
[52] U.S. Cl. .................. 424/324; 260/558 P; 260/558 S; 260/559 R; 260/559 A; 260/559 T
[58] Field of Search ............ 260/558 P, 559 R, 558 S, 260/559 A, 559 T; 424/324

[56] References Cited

U.S. PATENT DOCUMENTS

| | | | |
|---|---|---|---|
| 3,689,556 | 9/1972 | Welch et al. | 260/558 P |
| 3,825,594 | 7/1974 | Houlihan | 260/558 P X |
| 3,835,128 | 9/1974 | Bracha et al. | 260/558 P X |
| 3,859,443 | 1/1975 | Mrozik | 260/558 P |
| 3,880,924 | 4/1975 | Grier | 260/558 P |
| 3,975,435 | 8/1976 | Nikawjtz | 260/558 P |
| 4,048,227 | 9/1977 | Mowdood | 260/559 R X |
| 4,058,558 | 11/1977 | Cousse et al. | 260/558 P X |
| 4,058,558 | 11/1977 | Cousse et al. | 260/515 A |

FOREIGN PATENT DOCUMENTS

| | | | |
|---|---|---|---|
| 594496 | 3/1960 | Canada | 260/558 P |
| 512845 | 9/1939 | United Kingdom | 260/558 P |

OTHER PUBLICATIONS

Cramer et al., "J. Amer. Pharm. Assoc.," vol. 37, No. 11, pp. 439–449, (1948).
Awad et al., C.A. 77:101065v, (1972).

*Primary Examiner*—Winston A. Douglas
*Assistant Examiner*—John Doll
*Attorney, Agent, or Firm*—Walter Patton; Harry E. Westlake, Jr.

[57] ABSTRACT

Novel substituted benzoylacrylanilides are prepared by reacting a substituted benzoylacrylic acid with a substituted aniline in the presence of a coupling agent. These acrylanilides have significant anticoccidial activity.

25 Claims, No Drawings

SUBSTITUTED BENZOYLACRYLANILIDES

This is a continuation, of application Ser. No. 629,438 filed Nov. 6, 1975, now abandoned, which is a continuation-in-part of U.S. Ser. No. 521,708 filed Nov. 7, 1974 abandoned which in turn is a continuation-in-part of U.S. Ser. No. 416,134 filed Nov. 15, 1973, now abandoned.

DISCLOSURE OF THE INVENTION

This invention related to new and useful substituted benzoylacrylanilides, as well as to processes for their preparation. In addition, this invention relates particularly to the prevention and treatment of coccidiosis in poultry. More particularly, this invention is concerned with the effectiveness of variously substituted benzoylacrylanilides and with compositions containing these compounds for use in the prevention and treatment of coccidiosis.

Coccidiosis is a common and widespread poultry disease caused by a number of species of protozoan parasites of the genus *Eimeria*, including *E. tenella, E. necatrix, E. acervulina, E. maxima, E. hagani*, and *E. brunetti*. *E. tenella* is the causative agent of a severe and often fatal infection of the caeca of chickens, which is manifested by severe and extensive hemorrhage, accumulation of blood in the caeca, and the passage of blood in the droppings. *E. necatrix* attacks the small intestine of the chick causing what is known as intestinal coccidiosis. Related species of coccidia such as *E. meleagridis* and *E. adenoides* are causative organisms of coccidiosis in turkeys. When left untreated, the severe forms of coccidiosis lead to poor weight gain, reduced feed efficiency and high mortality in fowl. The elimination or control of this disease is important in order to insure protecting a valuable source of food protein.

Therefore, one object of this invention is to provide new compounds which possess coccidiostatic activity. Another object of this invention is to provide coccidiostatic compounds especially active against the species *E. tenella*. Still another object is to provide processes for the preparation of said compounds. A further object of this invention is to provide novel compositions containing these benzoylacrylanilides as an active ingredient. Additional objects will become apparent upon further reading of this description.

According to this invention, it has been found that substituted benzoylacrylanilides of formula I below are very effective in the prevention and treatment of coccidiosis.

$$\overset{O}{\underset{\|}{A-C}}-CH=CH-\overset{O}{\underset{\|}{C}}-NH-B \quad (I)$$

In the compounds of formula I, A represents:

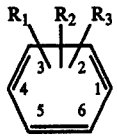

(a)

where in formula (a) $R_1$, $R_2$ and $R_3$ are independently hydrogen, halo, loweralkylsulfide, loweralkylsulfonyl, loweralkyl, loweralkoxy, loweralkanoylamino or trihaloloweralkyl.

In formula I above, B represents:

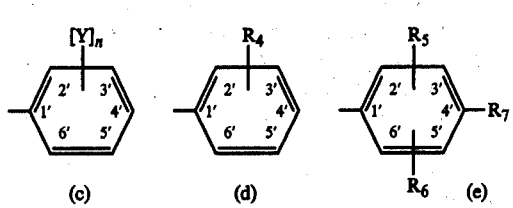

where in formula (c), Y is halo and n is an integer of 4 to 5; in formula (d), $R_4$ is halo, loweralkyl, loweralkoxy, loweralkylsulfide or trihaloloweralkyl; and in formula (e) $R_5$ and $R_6$ are independently hydrogen, loweralkyl, loweralkoxy, trihaloloweralkyl or halo and $R_7$ is halo, loweralkyl or hydrogen, and at least one or $R_5$, $R_6$ and $R_7$ being other than hydrogen with the provisos that when 1) A is mono-substituted at the para (4) position with hydrogen, loweralkyl, loweralkoxy or halo, $R_4$ is other than hydrogen, loweralkyl, loweralkoxy or halo at the para (4') position and at least one of $R_5$ and $R_6$ is other than hydrogen; and 2) further that in formula (e) when $R_5$ is 2'-loweralkyl, $R_6$ is 6'-loweralkyl, and $R_7$ is hydrogen, at least one of the $R_1$, $R_2$ and $R_3$ substituents in formula (a) is other than hydrogen or loweralkyl.

As used in this specification, the prefix, "lower" is meant to include groups having from 1 to 4 carbon atoms, e.g., methyl, ethyl, propyl and butyl, including the isomers of propyl and butyl. Also, in this specification the term, "halo" is intended to include fluoro, chloro, bromo and iodo.

Referring to those substituents comprising A of formula I, the preferred groups will depend on whether the phenyl groups of formula (a) above is mono-substituted or di-substituted.

When the phenyl groups of formula (a) is mono-substituted, that is where $R_1$ and $R_2$ are hydrogen then the preferred $R_3$ mono-substituents are loweralkoxy or loweralkylamino. Of the preferred mono-substituents, the most preferred are methoxy and acetamido.

When the phenyl groups of formula (a) are disubstituted that is where $R_1$ is hydrogen then the preferred $R_2$ and $R_3$ substituents are independently halo, loweralkoxy or loweralkyl. Of the preferred $R_2$ and $R_3$ substituents, the most preferred are chloro, methoxy or methyl.

Referring now to those substituents comprising B of formula I, it has been found that in formula (c), the preferred substituents include those where Y is chloro and n is 4 such that B is 2',3',5',6'-tetrachlorophenyl, and where Y is fluoro and n is 5 which is pentafluorophenyl.

In formula (d) $R_4$ is preferably loweralkyl. The most preferred substituent is methyl.

In formula (e) $R_7$ is fixed at the para (4') position and is preferably hydrogen. $R_5$ and $R_6$ are preferably hydrogen or loweralkyl. The most preferred loweralkyl is methyl. $R_5$ and $R_6$ can be in any position relative to each other or to its attachment to the amido nitrogen, but preferred are those compounds where $R_5$ and $R_6$ are in the 2'- and 6'-positions or the 3'- and 5'-positions.

A preferred group of substituted benzoylacrylanilides is where in formula (a) $R_1$, $R_2$ and $R_3$ are independently hydrogen, halo, loweralkyl, or loweralkoxy and wherein $R_4$, $R_5$, $R_6$ and $R_7$ are independently halo, hydrogen or loweralkyl.

A more preferred group of substituted benzoylacrylanilides is where in formula (a) $R_1$, $R_2$ and $R_3$ are hydrogen or halo and wherein $R_4$, $R_5$, $R_6$ and $R_7$ are independently loweralkyl or hydrogen.

The most preferred group of substituted benzoylacrylanilides is where in formula (a) $R_1$, $R_2$ and $R_3$ are independently hydrogen or chloro and $R_4$, $R_5$, $R_6$ and $R_7$ are independently methyl or hydrogen.

The preferred group of compounds of this invention are:
3-(3,4-dichlorobenzoyl)-2'-methylacrylanilide,
3-(3,4-dichlorobenzoyl)-2',6'-dimethylacrylanilide,
3-(3,5-dichlorobenzoyl)-2'-methylacrylanilide,
3-(3,5-dichlorobenzoyl)-2',6'-dimethylacrylanilide,
3-(3,4-dimethoxybenzoyl)-2'-methylacrylanilide,
3-(4-chloro-3-toluyl)-2'-methylacrylanilide,
3-(3-chloro-4-toluyl)-2'-methylacrylanilide,
3-(2,4-dichlorobenzoyl)-2'-methylacrylanilide,
3-(4-methoxybenzoyl)-2',6'-dimethylacrylanilide,
3-(4-acetamidobenzoyl)-2',6'-dimethylacrylanilide,
3-(4-methoxybenzoyl)-3',5'-dimethylacrylanilide,
3-(4-acetamidobenzoyl)-3',5'-dimethylacrylanilide,
3-(4-chloro-3-toluyl)-2',6'-dimethylacrylanilide,
3-(3-chloro-4-toluyl)-2',6'-dimethylacrylanilide,
3-(2,4-dichlorobenzoyl)-2',6'-dimethylacrylanilide,
3-(3,4-dichlorobenzoyl)-3',5'-dimethylacrylanilide,
3-(4-chloro-3-toluyl)-3',5'-dimethylacrylanilide,
3-(3-chloro-4-toluyl)-3',5'-dimethylacrylanilide, and
3-(2,4-dichlorobenzoyl)-3',5'-dimethylacrylanilide.

The most preferred group of compounds of this invention are the first four of the above group.

As described more fully below, these anticoccidial compounds are prepared by the reaction of an appropriately substituted benzoylacrylic acid,

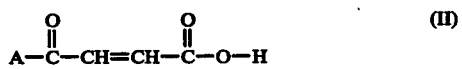

where A is as previously defined with an appropriate aniline derivative

where B is as previously defined in the presence of a coupling reagent such as dicyclohexylcarbodiimide, phosphorous oxychloride/triethylamine complex, and the like; or the reaction of a benzoylacrylhalide derived from an acid of formula II with a 2 to 5 molar excess of the aniline derivative.

As heretofore stated, it has now been found that the benzoylacrylanilides of this invention are highly active against protozoa responsible for coccidiosis, and hence are particularly useful in treating and preventing coccidiosis when administered to poultry. The active compounds are conveniently fed to poultry as a component of the feed of the animals although it may also be given dissolved or suspended in the drinking water. Although the compounds of this invention are effective against the many species of *Eimeria*, they are especially effective against *E. tenella*.

According to a preferred aspect of this invention, novel compositions for the treatment of coccidiosis are provided which comprises one or more substituted benzoylacrylanilides intimately dispersed in or intimately admixed with an inert edible carrier or diluent. By an inert edible carrier or diluent is meant one that is nonreactive with respect to the benzoylacrylanilide compound, and that may be administered with safety to the animals to be treated. The carrier or diluent is preferably one that is or may be an ingredient of the animal feed.

The compositions which are a preferred feature of this invention are the so-called feed supplements in which the substituted benzoylacrylanilides of this invention are present in relatively large amounts and which are suitable for addition to the poultry feed either directly or after an intermediate dilution or blending step. Examples of carriers or diluents suitable for such compositions are animal feed ingredients including edible vegetable substances such as distillers' dried grains, corn meal, citrus meal, fermentation residues, wheat shorts, molasses solubles, corn germ meal, corn cob meal, toasted dehulled soya flour, soybean mill feed, antibiotic mycelia, soya grits, and mineral substances such as ground oyster shells, Attapulgus clay, crushed dolomite and limestone. The benzoylacrylanilide compound is intimately dispersed or admixed throughout the solid inert carrier by methods such as grinding, stirring, milling, or tumbling. By selecting proper diluents and by altering the ratio of carrier to active ingredient, compositions of any desired concentration may be prepared. Formulations containing from about 1% to about 40% by weight and preferably from about 2-25% by weight, of the substituted benzoylacrylanilide are suitable as a feed supplement or so-called pre-mix which is intended for addition to poultry feedstuffs. Those having from about 5-20% by weight of coccidiostat are especially satisfactory for supplement compositions and are preferred. The active compound is usually dispersed or mixed uniformly in the diluent, but in some instances may be advantageously sorbed on the carrier. Since it is convenient for the feed manufacturer to use about one pound of feed supplement for each ton of finished feed, the preferred concentration in the supplement is usually a function of the level of active ingredient desired in the finished feed.

It is common practice to further dilute the feed supplements with materials such as corn meal or soybean meal before being incorporated in the animal feed. In this intermediate processing step the level of the compounds of this invention in the carrier is brought down to about 0.1% to 1.0% by weight. This dilution serves to facilitate uniform distribution of the coccidiostat in the finished feed. The finished feed is one that contains a source of fat, protein, carbohydrate, minerals, vitamins and other nutritional factors.

Very low levels of benzoylacrylanilide compounds in the ultimate feed are sufficient to afford the poultry good protection against coccidiosis. Suitably the compound is administered to chickens in an amount equal to about 0.0005% to 0.10% by weight of the daily feed intake. Preferred results are obtained by feeding at a level of about 0.001% to 0.05% by weight of the finished feed, and most preferably at a level of 0.0125% to 0.05% by weight. For therapeutic treatment of an established coccidial infection, higher amounts of substituted benzoylacrylanilides, i.e., up to about 0.1% by weight of the feed consumed, may be employed. The most advantageous level will, of course, vary somewhat with particular circumstances such as the type and severity of the coccidial infection to be treated and the likelihood of reinfection.

It will likewise be understood by those skilled in this art that special feed supplement formulations and finished animal feeds containing vitamins, antibiotics, growth-promoting agents and other nutritional substances may include one or more compounds of this invention. The following is a typical product of this type to which a compound of this invention can be added so as to comprise from 1% to 40% of the total weight.

| Ingredients: | Amount/lb. of Supplement, grains |
|---|---|
| Riboflavin | 0.64 g. |
| DL-calcium pantothenate | 2.10 |
| Niacin | 3.67 |
| Choline chloride | 50.00 |
| Vitamin $B_{12}$ concentrate | 1.30 mg. |
| Procaine penicillin | 0.84 g. |
| Vitamin A (100,000 u./g.) | 3.38 |
| Vitamin $D_3$ (200,000 u./g.) | 0.68 |
| Arsanilic acid | 18.36 |
| Butylated hydroxy toluene | 23.15 |
| DL-methionine | 23.15 |

Distillers' grains to 1 pound

Animal feed supplements having the following compositions are prepared by intimately mixing the benzoylacrylanilide and the particular edible solid diluent or diluents.

| | | Lbs. |
|---|---|---|
| A. | 3-(4-Chloro-3-toluoyl)-2',6'-dimethylacrylanilide | 7.5 |
| | Distillers' dried grains | 92.5 |
| B. | 3-(3,4-Dichlorobenzoyl)-2',6'-dimethylacrylanilide | 5.0 |
| | Soybean mill feed | 50.0 |
| | Fine soya grits | 45.0 |
| C. | 3-(3,4-Dimethoxybenzoyl)-2',6'-dimethylacrylanilide | 10.0 |
| | Molasses solubles | 90.0 |
| D. | 3-(3,4-Dichlorobenzoyl)-2',6'-dimethylacrylanilide | 15.0 |
| | Corn distillers' dried grains | 55.0 |
| | Corn germ meal | 30.0 |
| E. | 3-(2,4-Dichlorobenzoyl)-2',6'-dimethylacrylanilide | 20.0 |
| | Wheat shorts | 30.0 |
| | Corn distillers' dried grains | 50.0 |
| F. | 3-(4-Acetamidobenzoyl)-2',6'-dimethylacrylanilide | 25.0 |
| | Corn distillers' dried grains | 75.0 |
| G. | 3-(3,4-Dimethoxybenzoyl)-2',6'-dimethyl acrylanilide | 10.0 |
| | Nicarbazin | 15.0 |
| | Corn distillers' dried grains | 75.0 |

These supplements are made by mechanical milling or mixing of the ingredients to insure uniform distribution of the active compound.

This invention is not limited to coccidiostatic compositions having the benzoylacrylanilides as the sole active ingredient of this invention. Compositions may be prepared containing a compound of this invention admixed with one or more other coccidiostats such as sulfaquinoxaline, other sulfa compounds, 4,4'-dinitrocarbanilide/2-hydroxy-4,6-dimethylpyrimidine complex, 3,3'-dinitrodiphenyldisulfide, 5-nitrofurfural semicarbazone, amprolium, zoalene, buquinolate, ethopabate, Coydon, Cycostat, Coban, and the like. The combination of the substituted acrylanilides of this invention with 6-amino-substituted benzyl purines and their N-oxides as described in French Pat. No. 2,126,800, is, however, the invention of our colleagues, Brinton Miller and Edward McManus.

In the above discussion of this invention, emphasis has been placed on solid compositions wherein the active ingredient is mixed with an edible carrier in a feed supplement or in the final poultry feedstuff. This is the preferred method of administering the benzoylacrylanilide compound of this invention.

An alternate method of treatment is to dissolve or suspend the benzoylacrylanilide compound in the drinking water of animals. This method can be used to advantage in flocks having an established infection, because infected birds tend to consume less feed. The quantity of coccidiostat which may be administered in this fashion is, of course, limited by the solubility of the product in water or by the quantity that may be suspended in the water without undue settling. The preferred dose levels in the drinking water are usually somewhat less than those employed in a solid feed inasmuch as poultry drink about twice as much as they eat. A suitable level in drinking water is from 0.001% to 0.05% by weight of the substituted acrylanilide, the preferred range being from 0.001% to 0.025% by weight. For this purpose, it is convenient to prepare dispersible or water-soluble powders in which the substituted benzoylacrylanilide is intimately dispersed in a suitable water-soluble or dispersible liquid or solid carrier such as dextrose, sucrose, or other suitable non-toxic carriers, at concentrations of from about 0.03% to about 25% by weight with emulsifiers and surface active agents, if desired. These solids may then be conveniently added to the drinking water by the poultry grower.

A typical drinking water formulation contains 3-(3,4-dichlorobenzoyl)-2',6'-dimethylacrylanilide, 0.025%; dextrose, 30%; propylene glycol, 20%; dimethylpolysiloxane, 0.002%; polyoxyethylene sorbitan monoleate, 0.2%; water, to 100%.

The compounds of this invention are active anticoccidial agents and are employed in the above anticoccidial compositions are prepared by reacting the appropriately substituted benzoylacrylic acid with the appropriately substituted aniline in the presence of a coupling reagent. Most suitably, the benzoylacrylanilide is prepared by reaction of a solution of the corresponding benzoylacrylic acid and aniline with phosphorus oxychloride/triethylamine complex. The complex is best prepared *in situ*. The preferred procedure involves treating a tetrahydrofuran solution of one equivalent of the substituted benzoylacrylic acid and one equivalent of the substituted aniline with one equivalent of phosphorous oxychloride followed by the addition of two equivalents of triethylamine.

When electron withdrawing groups, or groups which greatly hinder reaction are present on the aniline compound, an improved yield is obtained by condensing the more reactive substituted benzoylacryl halides with an excess of the substituted aniline. Reactions of this type and the preparation of acyl halides are familiar to those skilled in the art utilizing halogenating agents such as phosphorous pentachloride or thionylchloride. Of the starting materials used for preparing the compounds of this invention the substituted aniline compounds are known.

Benzoylacrylic acid is also known, and the substituted benzoyl acrylic acids can be prepared from the appropriately substituted benzene by condensation with maleic anhydride. This reaction is performed by standard techniques utilized in conducting a Friedel-Crafts condensation employing the usual Lewis acid catalysts, especially aluminum chloride as outlined in Papa, Journal of the American Chemical Society, 70:3356 (1948), and Cramer, Journal of the American Pharmaceutical Association, 37:439 (1948).

When preparing substituted benzoylacrylic acids where the substituents present on the benzene reactant would tend to hinder its condensation with the maleic anhydride, it is preferable to employ the following preparative method. The substituted benzene is reacted with dichloroacetyl chloride, employing at least an equivalent amount of the diacetyl chloride. The reactants are admixed in the presence of a Lewis acid catalyst, such as, aluminum chloride. After reaction at 50° C. to 90° C. for a period of from 3-10 hours the substituted acetophenone is isolated. This in turn reacted with an alkali alkoxide suitably sodium methoxide in a suitable solvent such as methyl alcohol at room temperature. By suitable solvent is meant one which does not react irreversibly with reactants as products. After about 2 hours, the reaction is generally complete and the dialkoxy derivative isolated. Upon treatment with acid, the glyoxal hydrate is obtained and reacted by condensation with malonic acid followed by decarboxylation thereby forming the desired substituted benzoylacrylic acid. When preparing substituted benzoylacrylic acids where the substituents present on the benzene reactant would prevent condensation with maleic anhydride or produce an undesirable isomer of the substituted benzoylacrylic acid, it is preferable to employ the following preparative procedure. The corresponding substituted acetophenone in aqueous acetic acid is oxidized with an equivalent amount of selenium dioxide ($SeO_2$) at 50° C. to 150° C. for 178 to 3 hours. The corresponding substituted phenylglyoxal hydrate is isolated and converted to the benzoylacrylic acid as described above.

The following examples are set forth to illustrate the invention and are not to be construed as limitations thereon.

Preparation of Benzoylacrylic Acids

EXAMPLE 1

3-(4-Methylthiobenzoyl)acrylic Acid

A suspension of 66 g. (0.500 moles) of $AlCl_3$ in about 600 ml. of methylene chloride is stirred while 20 g. (0.20 moles) of maleic anhydride is added. The solution of the complex is decanted and is stirred while 25 g. (21 ml.) of methyl phenyl sulfide is added. The solution is refluxed for six hours and then left to stand overnight.

A solution of 100 ml. of concentrated HCl in one liter of ice water is added and the mixture stirred. The organic layer is then separated, washed with water, and extracted with aqueous sodium bicarbonate. The extract is washed with ether and then acidified with 6N HCl. The precipitate is filtered and washed with water.

The precipitate is dissolved in ethyl acetate, washed with water, dried, reduced to a small volume and diluted with hexane. The 3-(4-methylthiobenzoyl)acrylic acid is obtained in two crops 10 g. (23%), m.p. 162° C.-163° C.

EXAMPLE 2

3-(2,4,5-Trichlorobenzoyl)acrylic Acid

Step 1

A suspension of 40 g. (0.30 moles) of aluminum chloride in 200 ml. of tetrachloroethylene is treated with a solution of 28.8 ml. (44.2 g.; 0.30 moles) of dichloroacetylchloride in 30 ml. of tetrachloroethylene. The solution is stirred for 15 minutes and then 50 ml. (0.40 moles) of 1,2,4-trichlorobenzene is added. The mixture is then heated to 90° C. for six hours, then is poured into an ice-water mixture containing 90 ml. of concentrated HCl. The mixture is shaken and the aqueous phase extracted with methylene chloride. The extracts are added to the organic phase, washed with water and an aqueous solution of sodium bicarbonate, followed by a wash with a saturated sodium chloride solution. The solution is shaken with activated charcoal then filtered, concentrated to a residue and distilled under vacuum.

Step 2

The pentachloroacetophenone from Step 1 is added to a solution of 13 g. (0.241 moles) of sodium methoxide in 200 ml. of methanol. This mixture is refluxed for two hours, then cooled and filtered giving 7.8 g. solid. The filtrate is concentrated to a residue and taken up with methylene chloride and washed with 0° C. water, 2% HCl and saturated sodium chloride. The dried solution is treated with activated charcoal to give a residue of 20.8 g. Upon trituration with petroleum ether followed by filtration and stripping of solvent, 7.2 g. of crude product are obtained which after recrystallization from ether gave 4.1 g. The residue of 13 g. is chromatographed on silica gel and an additional 5.3 g. product is obtained.

Step 3

This 9.4 g. (0.033 mole) from Step 2 is dissolved in 60 ml. of dioxane and 60 ml. of 6N HCl is added. The mixture is then heated to 80° C. After 2 hours, the reaction mixture is cooled and extracted with methylene chloride, which extracts are combined and washed with saturated sodium chloride. There was obtained 9.3 g. of product.

Step 4

This product was dissolved in 25 ml. of pyridine and mixed with a solution of 3.75 g. (0.036 moles) of malonic acid in 25 ml. of pyridine. This reaction mixture is stirred overnight at room temperature. After 22 hours, the mixture is cooled and treated with 150 ml. of cold 5% $Na_2CO_3$. The solution is washed with benzene and methylene chloride and acidified with 6N HCl. The product is filtered, washed with water and recrystallized from ethyl acetatehexane. A total weight of 1.30 g. in three crops is obtained having a melting point of 177° C.-181° C.

EXAMPLE 3

3-(3,4-Dichlorobenzoyl)-2',6'-dimethylacrylanilide

A solution of 6.12 g. (0.025 moles) of 3,4-dichlorobenzoylacrylic acid and 4.0 ml. (3.94 g., 0.0325 moles) of 2,6-xylidine in 125 ml. of tetrahydrofuran is cooled to 5° C. and treated in succession with 3.0 ml. (5 g., 0.0328 moles) of $POCl_3$ and 10 ml. (7.25 g., 0.072 moles) of triethylamine. The temperature rises to 25° C. and then falls to 20° C. After stirring for one hour, the suspension mixture is diluted with water and stripped of solvent. A semi-crystalline solid is obtained which is washed with water, then slurried with ethyl acetate. After filtering and washing with ether, 2.8 g. of 3-(3,4-dichlorobenzoyl)-2',6'-dimethylacrylanilide is obtained having a melting point of 213° C.-215° C.

The following additional compounds are prepared by employing $POCl_3$ as a coupling reagent in accordance with the method of the above Example 3. An analogous quantity of the appropriate benzoylacrylic acid or substituted benzoylacrylic acid is employed in the manner of the 3,4-dichlorobenzoylacrylic acid of Example 3. Likewise, an analogous quantity of the appropriately substituted aniline is employed in the manner of 2,6-xylidine. Thus, to prepare 3-(benzoyl)-3′,5′-dimethylacrylanilide there is used an equivalent amount of benxoylacrylic acid in place of the 3,4-dichlorobenzoylacrylic acid and an equivalent amount of 3,5-xylidine in place of the 2,6-xylidine.

| Compounds | Melting Points |
|---|---|
| 3-(4-Trifluoromethylbenzoyl)-2′,6′-dimethylacrylanilide | 189°–191° C. |
| 3-(Benzoyl)-3′,5′-ditrifluoromethylacrylanilide | 175°–177° C. |
| 3-(3,4-Dichlorobenzoyl)-3′,5′-dimethylacrylanilide | 166°–167° C. |
| 3-(Benzoyl)-4′-chloroacrylanilide | 211°–213° C. |
| 3-(Benzoyl)-3′,5′-dimethylacrylanilide | 158°–159° C. |
| 3-(4-Chlorobenzoyl)-2′,6′-dimethylacrylanilide | 205°–207° C. |
| 3-(4-Bromobenzoyl)-2′,6′-dimethylacrylanilide | 211°–213° C. |
| 3-(2,3,4-Trichlorobenzoyl)-2′,6′-dimethylacrylanilide | 242°–248° C. |
| 3-(3,4-Dimethoxybenzoyl)-2′,6′-dimethylacrylanilide | 222°–225° C. |
| 3-(4-Methoxybenzoyl)-2′,6′-dimethylacrylanilide | 194°–195° C. |
| 3-(3-Methyl-4-chlorobenzoyl)-2′,6′-dimethylacrylanilide | 182°–184° C. |
| 3-(3-Acetamidobenzoyl)-2′,6′-dimethylacrylanilide | 276°–278° C. |
| 3-(2,4-Dichlorobenzoyl)-2′,6′-dimethylacrylanilide | 224°–226° C. |
| 3-(2,4,5-Trichlorobenzoyl)-2′,6′-dimethylacrylanilide | 238°–240° C. |
| 3-(Benzoyl)-3′,5′-dimethylacrylanilide | 160°–161° C. |
| 3-(Benzoyl)-4′-methoxyacrylanilide | 162°–164° C. |
| 3-(Benzoyl)-4′-trifluoromethylacrylanilide | 215°–217° C. |
| 3-(Benzoyl)-2′-methylacrylanilide | 168°–169° C. |
| 3-(Benzoyl)-4′-ethoxyacrylanilide | 167°–168° C. |
| 3-(Benzoyl)-4′-methylthioacrylanilide | 167°–168.5° C. |
| 3-(Benzoyl)-2′,4′,6′-trimethylacrylanilide | 212°–213° C. |
| 3-(Benzoyl)-2′,6′-diethylacrylanilide | 200°–202° C. |
| 3-(Benzoyl)-2′,6′-dimethoxyacrylanilide | 178° decomposes |
| cis 3-(Benzoyl)-2′,6′-dimethylacrylanilide | 143°–145° C. |
| 3-(3,4-Dichlorobenzoyl)-2′,3′,4′,5′,6′-pentafluoroacrylanilide | 202°–203° C. |
| 3-(3′4-dichlorobenzoyl)-2′-methylacrylanilide | 182°–183° C. |
| 3-(4-Methylbenzoyl)-2′,6′-dimethylacrylanilide | 195°–197° C. |
| 3-(3,4-Dichlorobenzoyl)-3′,5′-dimethoxyacrylanilide | 167°–169° C. |
| 3-(2,4-Dimethoxybenzoyl)-2′,6′-dimethylacrylanilide | 251° decomposes |
| 3-(2,5-Dimethoxybenzoyl)-2′,6′-dimethylacrylanilide | 183°–4° decomposes |
| 3-(4-Methoxy-3-methylbenzoyl)-2′,6′-dimethylacrylanilide | 228°–229° C. |
| 3-(2,4-Dichlorobenzoyl)-2′-methylacrylanilide | 206°–207° C. |
| 3-(3,4-Dimethoxybenzoyl)-2-methylacrylanilide | 165°–167° C. |
| 3-(2-Chloro-5-methylbenzoyl)-2′,6′-dimethylacrylanilide | 176°–178° C. |
| 3-(4-Chloro-2-methylbenzoyl)-2′,6′-dimethylacrylanilide | 180°–182° C. |
| 3-(3,4-Diethylbenzoyl-2′,6′-dimethylacrylanilide | 161°–163° C. |
| 3-(3-Chloro-4-methoxybenzoyl)2′,6′-dimethylacrylanilide | 221°–222° C. |
| 3-(3,4-Diethoxybenzoyl)-2′,6′-dimethylacrylanilide | 192°–193° C. |
| 3-(4-Fluoro-3-methylbenzoyl)-2′,6′-dimethylacrylanilide | 189°–190° C. |
| 3-(3,4-Dimethylbenzoyl)-2′,6′-dimethylacrylanilide | 183°–184° C. |
| 3-(5-Chloro-2-methoxybenzoyl)-2′,6′-dimethylacrylanilide | 206°–207° C. |
| 3-(3,4,5-Trimethoxybenzoyl)-2′,6′-dimethylacrylanilide | 182°–183° C. |
| 3-(4-Chloro-3-methylbenzoyl)-2′-methylacrylanilide | 155°–156° C. |
| 3-(4-Chloro-2-methylbenzoyl)-2′-methylacrylanilide | 155°–156° C. |
| 3-(3-Chloro-4-methoxybenzoyl)-2′-methylacrylanilide | 194°–196° C. |
| 3-(2-Methoxy-5-chlorobenzoyl)-2′-methylacrylanilide | 227°–228° C. decomposes |
| 3-(3,4-Diisopropoxybenzoyl)-2′,6′-dimethylacrylanilide | 163°–164° C. |

EXAMPLE 4

3-(4-Methylthiobenzoyl)-2′,6′-dimethylacrylanilide

A solution of 11 g. of the acid from Example 1 (0.050 moles) and 7.6 g. (0.062 moles) of 2,6-xylidine in 250 ml. of tetrahydrofuran was cooled to 5° C. and treated in rapid succession with 9.6 g. (0.062 moles) of $POCl_3$ and 13.6 g (0.136 moles) of triethylamine. This mixture is warmed to 23° C. with stirring for an hour, then diluted with water and concentrated to remove the tetrahydrofuran. The product is filtered and washed first with water, then with ethyl acetate and ether. There was obtained 7.8 g. of 3-(4-methylthiobenzoyl)-2′,6′-dimethylacrylanilide, a yield of 43% having a melting point of 216° C.–217° C.

EXAMPLE 5

3-(4-Methylsulfonyl)-2′,6′-dimethylacrylanilide

A suspension of 650 mg. (0.002 moles) of methylthioacrylanilide from Example 4 in 40 ml. of $CH_2Cl_2$ containing one ml. of methanol is treated with 890 mg. (0.0044 moles) of 85% m-chloroperbenzoic acid in 20 ml. of $CH_2Cl_2$. After standing overnight, the mixture containing a precipitate is stirred with 10 ml. of aqueous 10% $NaHCO_3$ and filtered. The solid is washed with water and the filtrate separated. The organic phase is washed with water. The original precipitate is dissolved in methylene chloride and the solution combined with the original methylene chloride solution. These solutions are filtered, and then partially stripped of solvent, and diluted with hexane. There was obtained 540 mg. of 3-(4-methylsulfonyl)-2′,6′-dimethylacrylanilide having a melting point of 222° C.–228° C.

EXAMPLE 6

3-Benzoyl-2′,6′-dichloroacrylanilide

A stream of nitrogen is passed through a flask containing 12.5 g., phosphorous pentachloride. With cooling and agitation, 10.6 g. (0.060 moles) of 3-benzoylacrylic acid is added. After a vigorous evolution of hydrogen chloride and with continued cooling the reaction mixture forms a homogeneous liquid which is stirred for an additional 15 minutes. To the reaction mixture is then added 150 ml. of diethyl ether followed by 38.9 g. (0.24 moles) of 2,6-dichloroaniline. The reaction mixture is stirred for an additional ½ hour and then allowed to return to room temperature over a 2½ hour period. Then the reaction mixture is treated with an ice and water mixture. The reaction mixture is stirred vigorously for 20 minutes and the solids then filtered and washed with water followed by an ether wash. The solids are taken up with $CHCl_3$, dried over magnesium sulfate, and then concentrated under vacuum to dryness. The yield is 5.8 g. of product and having a melting point of 198° C.–201° C. This product was additionally purified by slurrying in 50 ml. of $CHCl_3$ followed by filtration and washing with additional CHCl₃. This yields 4.33 g. of product having a melting point of 207° C.-208° C.

The following additional compounds are prepared by employing PCl₅ reagent in accordance with the method of the above Example 6. An analogous quantity of the appropriate benzoylacrylic acid or a substituted benzoylacrylic acid is employed in the manner of the benzoylacrylic acid of Example 5. Likewise, an analogous quantity of the appropriately substituted aniline is employed in the manner of the 2,6-dichloroaniline. Thus, to prepare 3-(benzoyl)pentafluoroacrylanilide, an analogous amount of benzoylacrylic acid is employed and there is used an analogous quantity of pentafluoroaniline in place of the 2,6-dichloroaniline.

| Compounds | Melting Points |
|---|---|
| 3-(Benzoyl)pentafluoroacrylanilide | 167°–169° C. |
| 3-(Benzoyl)-2',4',6'-trichloroacrylanilide | 214°–215° C. |
| 3-(Benzoyl)-2',4',5',6'-tetrachloroacrylanilide | 214°–216° C. |
| 3-(Benzoyl)-2',6'-dibromoacrylanilide | 243°–244° C. |
| 3-(Benzoyl)-2',6'-dimethyl-4-nitroacrylanilide | 221°–222° C. |
| 3-(3,4-Dichlorobenzoyl)-2',6'-dichloroacrylanilide | 204°–206° C. |

EXAMPLE 7

To determine the anticoccidial activity of the compounds of this invention, the following method is employed. Cecal coccidiosis is produced in 2-week old chicks by means of weighing straight-run white Leghorn chicks, and placing in cages with wire floors (then in groups of three). The chicks are fed *ad libitum* a standard laboratory ration in which 0.1% prolintane HCl is blended immediately prior to use. Nicarbazin and amprolium are used as reference standards. Control groups of normal and infected birds are fed basal ration alone. On the second day of test the chicks are each orally inoculated with 50,000 sporulated oocysts of *Eimeria tenella*. Papers under the cages are examined on the sixth, seventh and eighth days of the test for bloody droppings. A score of 0 is given if bloody spots are not observed; scores of 1, 2 or 4 were assigned for 1-3, 4-6 and > 6 bloody spots, respectively. On the eighth day of the test, the surviving birds are weighed, sacrificed and examined grossly for cecal coccidiosis lesions. Normal ceca are scored 0 and ceca with detectable, moderate and maximal lesions are scored 1, 2 and 4, respectively. When a bird dies and cecal coccidiosis lesions are present, a score of 5 is recorded. Compounds are rated on the basis of the total scores for bloody spots and cecal lesions as follows: A, active, 0-3; MA, moderately active, 4-7; SA, slightly active, 8-10; and inactive, > 10. Weight gain is indicated as good (G) or fair (F). Below the dosage levels indicated, some evidence of inactivity is encountered.

Illustrative results include:

| Compounds | Doses (%) in Ration | Anti-E. tenella Activities | Weight Gains |
|---|---|---|---|
| 3-(3,5-Dichlorobenzoyl)-2'-methylacrylanilide | 0.0125 | A | — |
| 3-(3,5-Dichlorobenzoyl)-3',5'-dimethylacrylanilide | 0.0125 | MA | — |
| 3-(4-Methoxybenzoyl)-2',6'-dimethylacrylanilide | 0.0125 | A | — |
| 3-(4-Chloro-2-toluyl)-2',6'-dimethylacrylanilide | 0.0125 | A | — |
|  | 0.006 | MA | — |
| 3-(3,4-Dimethoxybenzoyl)-2',6'-dimethylacrylanilide | 0.0125 | A | — |
|  | 0.006 | A | — |
| 3-(4-Acetamidobenzoyl)-2',6'-dimethylacrylanilide | 0.0125 | A | — |
|  | 0.006 | SA | — |
| 3-(2,4-Dichlorobenzoyl)-2',6'-dimethylacrylanilide | 0.0125 | A | — |
|  | 0.006 | A | — |
|  | 0.003 | SA | — |
| 3-(Benzoyl)-3',5'-dimethylacrylanilide | 0.05 | A | F |
|  | 0.025 | A | G |
|  | 0.0125 | SA | F |
| 3-(Benzoyl)-2',6'-dichloroacrylanilide | 0.0125 | A | G |
|  | 0.006 | MA | G |
| 3-(Benzoyl)-2',3',4',5',6'-pentafluoroacrylanilide | 0.050 | A | G |
|  | 0.025 | A | G |
|  | 0.0125 | MA | G |
|  | 0.006 | SA | G |
|  | 0.003 | SA | G |
| 3-(Benzoyl)-3',5'-acrylanilide | 0.050 | A | G |
|  | 0.0125 | MA | G |
| 3-(3,4-Dichlorobenzoyl)-2',6'-dimethylacrylanilide | 0.050 | A | F |
|  | 0.025 | A | G |
|  | 0.0125 | A | G |
| 3-(Benzoyl)-2',4',6'-trichloroacrylanilide | 0.05 | A | G |
| 3-(Benzoyl)-2',6'-dibromoacrylanilide | 0.05 | A | F |

EXAMPLE 8

In order to illustrate the activity against a field strain of *E. tenella* such as would be encountered by commercially raised chickens, the following method is employed.

Two-week-old sex and weight balanced white cross chicks caged in groups of 8 to 10 are fed a standard commercial ration to which drugs are added just prior to use. The uninfected and infected control birds are fed the basal ration. On the second day of the test the chicks are inoculated orally with a number of sporulated oocysts of *E. tenella* sufficient to produce significant mortality in non-medicated control groups.

Several criteria are employed for evaluation of anticoccidial efficacy of a drug. These include observations and records on the mortality rate, growth, severity of pathological lesions and number of oocysts produced. Coccidial lesions are scored according to the following system: 0= normal, 1= detectable, 2= moderate, 3= marked and 4= maximal. To obtain estimates of oocyst production, the ceca are homogenized in a blender. Appropriate aliquots are diluted, placed in a hemocytometer and counted. Oocyst counts are scored based on relative % of counts of infected unmedicated controls. Growth rates are evaluated based on relative % growth of uninfected unmedicated controls.

The results are recorded in the following Table I.

TABLE I
EFFICACY OF 3-BENZOYLACRYLAMIDES VS. E. TENELLA (FIELD STRAIN)

| Sample No. | Percent in Diet | Absolute Wt. Gain | Gross Lesion Score | Oocysts Million/ Bird | Survival Rate | Relative Wt. Gain |
|---|---|---|---|---|---|---|
| Normal Ave. | — | 111.7 | 0.0 | 0.0 | 100 | 100 |
| Infected Ave. | — | 75.4 | 4.0 | 44.5 | 26 | 67 |

TABLE I-continued
EFFICACY OF 3-BENZOYLACRYLAMIDES VS. E. TENELLA (FIELD STRAIN)

| Sample No. | Percent in Diet | Absolute Wt. Gain | Gross Lesion Score | Oocysts Million/ Bird | Survival Rate | Relative Wt. Gain |
|---|---|---|---|---|---|---|
| 3-(Benzoyl)-2',6'-dichloroacrylanilide | 0.05 | 121.1 | 0.0 | 0.1 | 100 | 108 |
|  | 0.025 | 127.5 | 0.0 | 0.5 | 100 | 114 |
|  | 0.0125 | 114.9 | 1.6 | 4.4 | 100 | 103 |
|  | 0.006 | 110.4 | 2.1 | 16.3 | 100 | 99 |
| 3-(Benzoyl)-3',5'-dimethylacrylanilide | 0.05 | 116.6 | 0.0 | 0.2 | 100 | 104 |
|  | 0.025 | 131.4 | 0.3 | 3.1 | 100 | 118 |
|  | 0.0125 | 117.6 | 1.6 | 9.0 | 100 | 105 |
|  | 0.006 | 103.4 | 3.3 | 19.6 | 100 | 93 |
| 3-(Benzoyl)-pentafluoroacrylanilide | 0.05 | 120.7 | 0.1 | 0.9 | 100 | 108 |
|  | 0.025 | 118.9 | 0.6 | 5.6 | 100 | 106 |
|  | 0.0125 | 124.0 | 1.3 | 6.7 | 100 | 111 |
|  | 0.006 | 92.6 | 2.9 | 14.5 | 100 | 83 |
| 3-(3,4-dichlorobenzoyl)-2',6'-dimethylacrylanilide | 0.05 | 121.6 | 0.0 | 0.0 | 100 | 109 |
|  | 0.025 | 120.9 | 0.0 | 0.1 | 100 | 108 |
|  | 0.0125 | 117.0 | 0.0 | 1.5 | 100 | 105 |
|  | 0.006 | 108.0 | 1.4 | 5.3 | 100 | 97 |

Now having described this invention, it will be understood that any departure from the above description which conforms to the invention is intended to be included within the scope of the claims.

What is claimed is:

1. A compound of the formula:

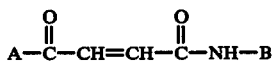

where A is:

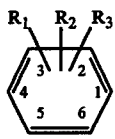

where in formula (a) $R_1$, $R_2$ and $R_3$ are independently hydrogen, halo, loweralkylsulfide, loweralkylsulfonyl, loweralkyl, loweralkoxy, loweralkanoylamino or trihaloloweralkyl;

In formula I above, B represents:

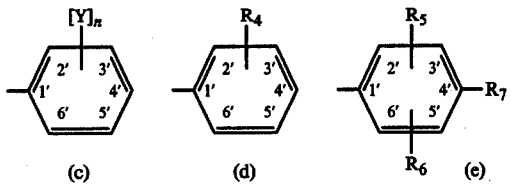

where in formula (c), Y is halo and n is an integer of 4 to 5; in formula (d), $R_4$ is halo, loweralkyl, loweralkoxy, loweralkylsulfide or trihaloloweralkyl; and in formula (e) $R_5$ and $R_6$ are independently hydrogen, loweralkyl, loweralkoxy, trihaloloweralkyl or halo and $R_7$ is halo, loweralkyl or hydrogen, and at least one of $R_5$, $R_6$ and $R_7$ being other than hydrogen with the provisos that when 1) A is mono-substituted at the para (4) position with hydrogen, loweralkyl, loweralkoxy or halo, $R_4$ is other than hydrogen, loweralkyl, loweralkoxy or halo at the para (4') position, and at least one of $R_5$ and $R_6$ is other than hydrogen; and 2) further that in formula (e) when $R_5$ is 2-loweralkyl, $R_6$ is 6-loweralkyl, and $R_7$ is hydrogen, at least one of the $R_1$, $R_2$ and $R_3$ substituents in formula (a) is other than hydrogen or loweralkyl.

2. A compound according to claim 1 wherein $R_1$ and $R_2$ are hydrogen and $R_3$ is loweralkoxy or loweralkylamino.

3. A compound according to claim 2 wherein $R_3$ is methoxy or acetamido.

4. A compound according to claim 1 wherein Y is chloro or fluoro.

5. A compound according to claim 1 wherein $R_4$ is loweralkyl.

6. A compound according to claim 5 wherein $R_4$ is methyl.

7. A compound according to claim 1 wherein $R_5$ and $R_6$ are hydrogen or loweralkyl and $R_7$ is hydrogen.

8. A compound according to claim 7 wherein $R_5$ and $R_6$ are loweralkyl.

9. A compound according to claim 7 wherein $R_5$ is loweralkyl and $R_6$ is hydrogen.

10. A compound according to claim 1 wherein $R_1$ is hydrogen and $R_2$ and $R_3$ are independently halo, loweralkoxy or loweralkyl.

11. A compound according to claim 10 wherein $R_2$ and $R_3$ are chloro, methoxy or methyl.

12. A compound according to claim 1 wherein $R_1$ and $R_2$ are hydrogen, $R_3$ is loweralkoxy or loweralkylamino, $R_5$ and $R_6$ are hydrogen or loweralkyl and $R_7$ is hydrogen.

13. A compound according to claim 1 wherein $R_1$, $R_2$ or $R_3$ are independently hydrogen or chloro and $R_5$, $R_6$ or $R_7$ are independently methyl or hydrogen.

14. A compound according to claim 13 which is 3-(3,4-dichlorobenzoyl)-2'-methylacrylanilide.

15. A compound according to claim 12 which is 3-(4-acetamidobenzoyl)-2',6'-dimethylacrylanilide.

16. A compound according to claim 12 which is 3-(4-methoxybenzoyl)-2',6'-dimethylacrylanilide.

17. A compound according to claim 1 selected from the group consisting of:
3-(3,4-dimethoxybenzoyl)-2'-methylacrylanilide,
3-(3,4-dichlorobenzoyl)-2'-methylacrylanilide,
3-(4-chloro-3-toluyl)-2'-methylacrylanilide,
3-(3-chloro-4-toluyl)-2'-methylacrylanilide,
3-(2,4-dichlorobenzoyl)-2'-methylacrylanilide,
3-(3,5-dichlorobenzoyl)-2'-methylacrylanilide,
3-(3,5-dichlorobenzoyl)-2',6'-dimethylacrylanilide,
3-(4-methoxybenzoyl)-2',6'-dimethylacrylanilide,
3-(4-acetamidobenzoyl)-2',6'-dimethylacrylanilide,
3-(4-methoxybenzoyl)-3',5'-dimethylacrylanilide,
3-(4-acetamidobenzoyl)-3',5'-dimethylacrylanilide,
3-(3,4-dichlorobenzoyl)-2',6'-dimethylacrylanilide,
3-(4-chloro-3-toluyl)-2',6'-dimethylacrylanilide,
3-(3-chloro-4-toluyl)-2',6'-dimethylacrylanilide,
3-(2,4-dichlorobenzoyl)-2',6'-dimethylacrylanilide,
3-(3,4-dichlorobenzoyl)-3',5'-dimethylacrylanilide,
3-(4-chloro-3-toluyl)-3',5'-dimethylacrylanilide,
3-(3-chloro-4-toluyl)-3',5'-dimethylacrylanilide, and
3-(2,4-dichlorobenzoyl)-3',5'-dimethylacrylanilide.

18. A compound according to claim 1 selected from the group consisting of:
3-(3,4-dichlorobenzoyl)-2'-methylacrylanilide,
3-(3,4-dichlorobenzoyl)-2',6'-dimethylacrylanilide, 3-(3,5-dichlorobenzoyl)-2'-methylacrylanilide, and
3-(3,5-dichlorobenzoyl)-2',6'-dimethylacrylanilide.

19. A composition for the treatment of coccidiosis comprising an inert carrier and an anticoccidal amount of a compound of the formula:

$$A-\overset{O}{\underset{\|}{C}}-CH=CH-\overset{O}{\underset{\|}{C}}-NH-B \qquad (I)$$

where A is:

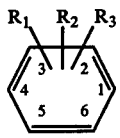 (a)

where in formula (a) $R_1$, $R_2$ and $R_3$ are independently hydrogen, halo, loweralkylsulfide, loweralkylsulfonyl, loweralkyl, loweralkoxy, loweralkanoylamino or trihaloloweralkyl;

In formula I above, B represents:

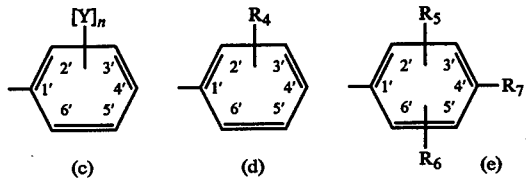

where in formula (c), Y is halo and n is an integer of 4 to 5; in formula (d), $R_4$ is halo, loweralkyl, loweralkoxy, loweralkylsulfide or trihaloloweralkyl; and in formula (e) $R_5$ and $R_6$ are independently hydrogen, loweralkyl, loweralkoxy, trihaloloweralkyl or halo and $R_7$ is halo, loweralkyl or hydrogen, and at least one of $R_5$, $R_6$ and $R_7$ being other than hydrogen with the provisos that when 1) A is mono-substituted at the para (4) position with hydrogen, loweralkyl, loweralkoxy or halo, $R_4$ is other than hydrogen, loweralkyl, loweralkoxy or halo at the para (4') position, and at least one of $R_5$ and $R_6$ is other than hydrogen; and 2) further that in formula (e) when $R_5$ is 2-loweralkyl, $R_6$ is 6-loweralkyl, and $R_7$ is hydrogen, at least one of the $R_1$, $R_2$ and $R_3$ substituents in formula (a) is other than hydrogen or loweralkyl.

20. A composition according to claim 19 where said compound comprises from 0.0005% to 0.10% by weight of said composition.

21. A composition according to claim 19 where said compound is selected from the group consisting of:
3-(3,4-dimethoxybenzoyl)-2'-methylacrylanilide,
3-(3,4-dichlorobenzoyl)-2'-methylacrylanilide,
3-(4-chloro-3-toluyl)-2'-methylacrylanilide,
3-(3-chloro-4-toluyl)-2'-methylacrylanilide,
3-(2,4-dichlorobenzoyl)-2'-methylacrylanilide,
3-(3,5-dichlorobenzoyl)-2'-methylacrylanilide,
3-(3,5-dichlorobenzoyl)-2',6'-dimethylacrylanilide,
3-(4-methoxybenzoyl)-2',6'-dimethylacrylanilide,
3-(4-acetamidobenzoyl)-2',6'-dimethylacrylanilide,
3-(4-methoxybenzoyl)-3',5'-dimethylacrylanilide,
3-(4-acetamidobenzoyl)-3',5'-dimethylacrylanilide,
3-(3,4-dichlorobenzoyl)-2',6'-dimethylacrylanilide,
3-(4-chloro-3-toluyl)-2',6'-dimethylacrylanilide,
3-(3-chloro-4-toluyl)-2',6'-dimethylacrylanilide,
3-(2,4-dichlorobenzoyl)-2',6'-dimethylacrylanilide,
3-(3,4-dichlorobenzoyl)-3',5'-dimethylacrylanilide,
3-(4-chloro-3-toluyl)-3',5'-dimethylacrylanilide,
3-(3-chloro-4-toluyl)-3',5'-dimethylacrylanilide, and
3-(2,4-dichlorobenzoyl)-3',5'-dimethylacrylanilide,
and comprises from 0.0005% to 0.10% by weight of said composition.

22. A composition according to claim 19 where said compound is selected from the group consisting of:
3-(3,4-dichlorobenzoyl)-2'-methylacrylanilide,
3-(3,4-dichlorobenzoyl)-2',6'-dimethylacrylanilide,
3-(3,5-dichlorobenzoyl)-2'-methylacrylanilide, and
3-(3,5-dichlorobenzoyl)-2',6'-dimethylacrylanilide
and comprises from 0.0005% to 0.10% by weight of said composition.

23. A composition according to claim 19 where said composition is a feed premix and said compound comprises from 2% to 25% by weight of the premix.

24. A composition according to claim 19 where said composititon is a feed premix and said compound is selected from the group consisting of:
3-(3,4-dimethoxybenzoyl)-2'-methylacrylanilide,
3-(3,4-dichlorobenzoyl)-2'-methylacrylanilide,
3-(4-chloro-3-toluyl)-2'-methylacrylanilide,
3-(3-chloro-4-toluyl)-2'-methylacrylanilide,
3-(2,4-dichlorobenzoyl)-2'-methylacrylanilide,
3-(3,5-dichlorobenzoyl)-2'-methylacrylanilide,
3-(3,5-dichlorobenzoyl)-2',6'-dimethylacrylanilide,
3-(4-methoxybenzoyl)-2',6'-dimethylacrylanilide,
3-(4-acetamidobenzoyl)-2',6'-dimethylacrylanilide,
3-(4-methoxybenzoyl)-3',5'-dimethylacrylanilide,
3-(4-acetamidobenzoyl)-3',5'-dimethylacrylanilide,
3-(3,4-dichlorobenzoyl)-2',6'-dimethylacrylanilide,
3-(4-chloro-3-toluyl)-2',6'-dimethylacrylanilide,
3-(3-chloro-4-toluyl)-2',6'-dimethylacrylanilide,
3-(2,4-dichlorobenzoyl)-2',6'-dimethylacrylanilide,
3-(3,4-dichlorobenzoyl)-3',5'-dimethylacrylanilide,
3-(4-chloro-3-toluyl)-3',5'-dimethylacrylanilide,
3-(3-chloro-4-toluyl)-3',5'-dimethylacrylanilide, and
3-(2,4-dichlorobenzoyl)-3',5'-dimethylacrylanilide
and comprises from 2% to 25% by weight of the premix.

25. A composition according to claim 19 where said composition is a feed premix and said compound is selected from the group consisting of:
3-(3,4-dichlorobenzoyl)-2'-methylacrylanilide,
3-(3,4-dichlorobenzoyl)-2',6'-dimethylacrylanilide,
3-(3,5-dichlorobenzoyl)-2'-methylacrylanilide, and
3-(3,5-dichlorobenzoyl)-2',6'-dimethylacrylanilide
and comprises from 2% to 25% by weight of the premix.

* * * * *

UNITED STATES PATENT OFFICE
CERTIFICATE OF CORRECTION

Patent No. 4,130,661  Dated December 19, 1978

Inventor(s) Peter Kulsa, Dale R. Hoff & Helmut H. Mrozik

It is certified that error appears in the above-identified patent and that said Letters Patent are hereby corrected as shown below:

Column 7, line 29 - Delete "178" and add ---1/2---.

Signed and Sealed this

Sixth Day of March 1979

[SEAL]

Attest:

RUTH C. MASON
*Attesting Officer*

DONALD W. BANNER
*Commissioner of Patents and Trademarks*